United States Patent [19]
Craig

[11] Patent Number: 5,401,636
[45] Date of Patent: Mar. 28, 1995

[54] ENHANCED SENSITIVITY AGGLUTINATION ASSAYS MULTIVALENT LIGANDS

[75] Inventor: Alan R. Craig, Wilmington, Del.

[73] Assignee: E. I. Du Pont de Nemours and Company, Wilmington, Del.

[21] Appl. No.: 156,169

[22] Filed: Nov. 23, 1993

Related U.S. Application Data

[63] Continuation of Ser. No. 964,312, Oct. 21, 1992, abandoned.

[51] Int. Cl.⁶ .................... C12Q 1/68; G01N 33/546
[52] U.S. Cl. ........................ 435/6; 435/7.21; 435/965; 436/524; 436/528; 436/531; 436/532; 436/533; 436/534
[58] Field of Search ............... 435/6, 7.21, 7.93, 965; 436/524, 528, 531, 532, 533, 534, 164, 909

[56] References Cited

U.S. PATENT DOCUMENTS

| | | | |
|---|---|---|---|
| 4,064,080 | 12/1977 | Daniel | 260/8 |
| 4,181,636 | 1/1980 | Fischer | 260/8 |
| 4,210,723 | 7/1980 | Dorman et al. | 435/180 |
| 4,401,765 | 8/1983 | Craig et al. | 436/533 |
| 4,480,041 | 10/1984 | Myles et al. | 436/508 |
| 4,703,018 | 10/1987 | Craig et al. | 436/518 |
| 4,772,550 | 9/1988 | Greenquist | 435/7 |
| 4,829,011 | 5/1989 | Gibbons | 436/512 |

FOREIGN PATENT DOCUMENTS

3785289 4/1989 Australia.

Primary Examiner—Esther M. Kepplinger
Assistant Examiner—Susan C. Wolski

[57] ABSTRACT

An agglutination-based method for detecting and/or an analyte by allowing the agglutination reaction between the analyte, a carrier reagent, and an agglutinating agent to occur in the presence of a multivalent ligand.

10 Claims, 3 Drawing Sheets

ENHANCED SENSITIVITY AGGLUTINATION ASSAYS MULTIVALENT LIGANDS

This is a continuation of application Ser. No. 07/964,312, filed Oct. 21, 1992, now abandoned.

TECHNICAL FIELD

This invention relates generally to an agglutination based method to detect and/or quantitate an analyte in a sample and, more particularly, to an enhanced sensitivity agglutination assay in which the agglutination reaction between an analyte, a carrier reagent which is a specific binding substance attached to a carrier, and an agglutinating agent, is performed in the presence of a multivalent ligand having at least two binding sites which are capable of specifically binding with the same binding site on an agglutinating agent.

BACKGROUND ART

Agglutination based processes have been used in qualitative and quantitative assays for a wide variety of bacteria, cell-surface antigens, and serum proteins, as well as several other analytes of interest. An example of a well known agglutination reaction is the reaction of bivalent antibodies with multivalent antigens to produce aggregates which can be detected and/or measured in a variety of ways. Compounds having multiepitopic receptors are capable of agglutinating particles coated with antigens or antibodies to produce agglomerates. These agglomerates can subsequently be detected using light scattering measurements.

In order to produce large, crosslinked aggregates in the agglutination reaction between bivalent antibodies and antigens, the antigens should have at least two or more specific binding sites. When the detection of monovalent haptens is desired, the reaction scheme can be modified by first preparing a multivalent form of the hapten, such as a hapten-protein conjugate. Consequently, any hapten present in a sample must compete with its multivalent form for the available specific binding sites of the antibody, resulting in a corresponding reduction of the measured amount of agglutination. Known methods for the preparation of multivalent forms of haptens include methods used to bind haptens to carriers in the preparation of immunogens.

The use of particles as carriers for the analyte, rather than the use of soluble proteins or protein conjugates as carriers, for enhanced sensitivity of visual or instrumental detection and/or measurement of agglutination or its inhibition is known. For example, a typical method used to attach particles to antibodies for use as particle reagents is adsorption of the antibodies onto the surface of suitable adsorbents. Polystyrene-based latex particles have been used extensively for this purpose.

Alternatively, particle reagents can be prepared by covalent attachment of the analyte to the surface of the particles. Polystyrene polymers have been modified to include functional groups capable of covalent protein attachment. U.S. Pat. No. 4,064,080 issued Dec. 20, 1977 discloses proteins covalently attached to styrene polymers via terminal amino phenyl groups. U.S. Pat. No. 4,181,636, issued Jan. 1, 1980, discloses carboxylated latex polymers coupled to immunologically active materials through a water soluble activating agent and their use as diagnostic reagents in agglutination tests. U.S. Pat. No. 4,210,723, issued Jul. 1, 1980, describes shell-core latex polymer particles of 0.15–1.5 µm diameter having epoxy groups on the surface of the particles and the coupling of proteins through these epoxy groups. U.S. Pat. Nos. 4,401,765, issued Aug. 30, 1983 and 4,480,041, issued Oct. 30, 1984 disclose covalently bonded high refractive index particle reagents and their use in light scattering immunoassays. U.S. Pat. No. 4,703,018, issued Oct. 27, 1987, discloses high refractive index haloalkyl-functional shell-core polymers and their use in immunoassays where the shell-core polymers are covalently bonded to compounds of biological interest.

Agglutination assays are typically conducted in an inhibition format for the detection of antigens and haptens suspected to be present in liquid samples. Usually, the binding of a multivalent antibody to highly refractive particles coated with a specific binding antigen or hapten is inhibited in a competitive fashion by the antigen or hapten in the test sample (see for example, U.S. Pat. No. 4,401,765, issued Aug. 30, 1983). However, these assays are generally limited in sensitivity to antigens and haptens in the concentration range of $10^{-7}$ to $10^{-10}$ molar. Thus, while particle reagents composed of particle carriers and attached proteins provide a means for agglutination-based assays, assays such as latex particle carrier based assays often do not provide the sensitivity required for analytes present at sub-nanomolar concentrations. A continuing problem in agglutination-based immunoassays is the inability to detect analytes at concentrations below $10^{-10}$ molar.

Australian Patent Application No. 37852/89, published Jan. 11, 1990, discloses a method for the detection of a specific binding substance (SBS) which includes incubating the specific binding substance with at least three receptors; R1 and R2 which can bind to each other and R3 which specifically binds SBS, and measuring the resulting agglutination. R1 is a conjugate of one component of a specific binding pair (P) with a substance which is SBS or its analog and having at least one epitope in common; R2 has at least two binding sites for P and R3 has at least two binding sites, at least one of which binds specifically to an epitope of the SBS. Australian Patent Application No. 37852/89 does not disclose the use of a multivalent ligand having at least two binding sites which are capable of specifically binding with the same binding site on an agglutinating agent.

SUMMARY OF THE INVENTION

Figure 1:
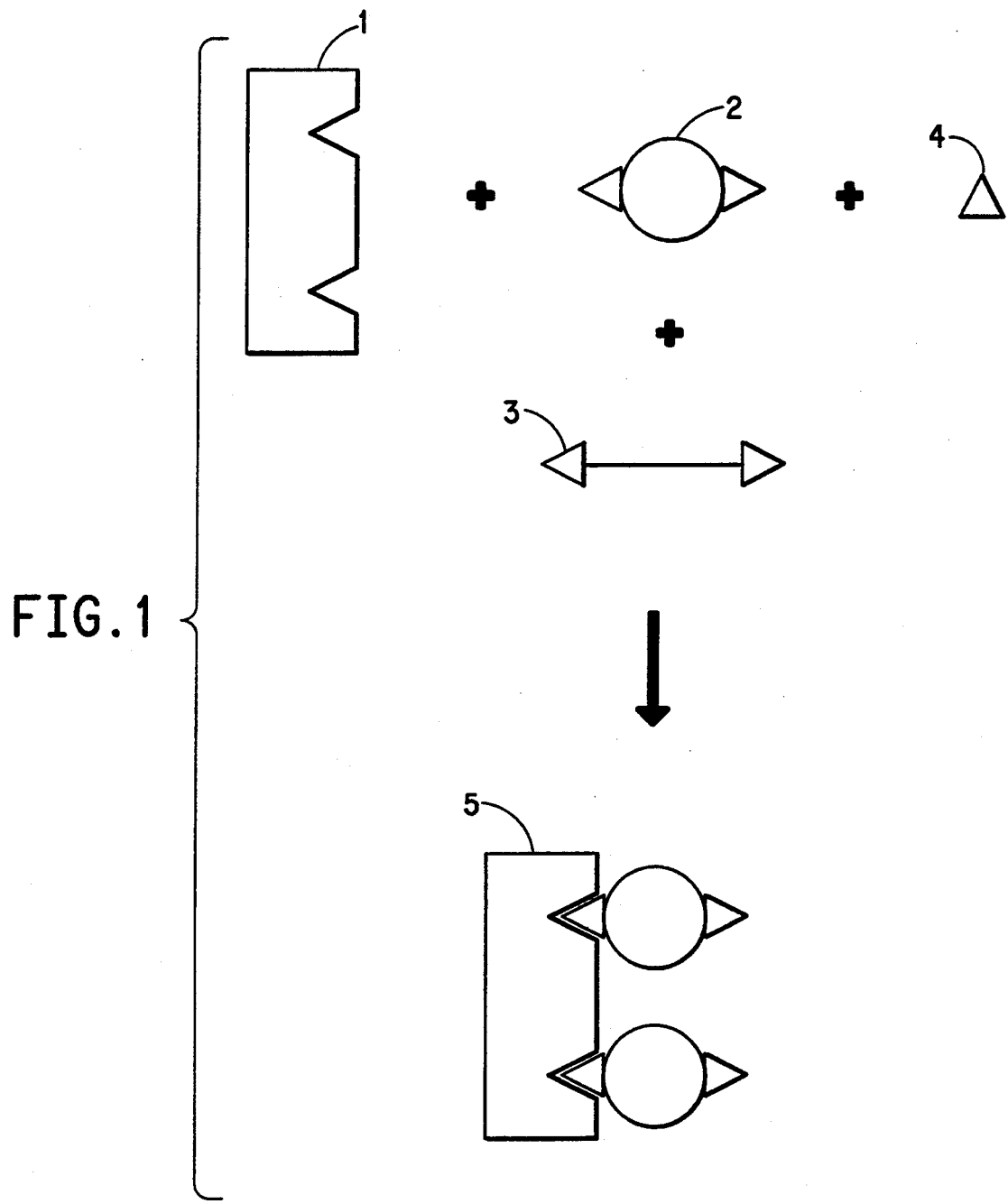
FIG. 1 is a schematic representation of the present invention for detecting and/or quantitating an analyte.

This invention relates to a method to detect and/or quantitate an analyte in a sample which comprises:
(A) incubating
   (a) a sample suspected of containing an analyte,
   (b) a carrier reagent, wherein the carrier reagent is a specific binding substance attached to a carrier;
   (c) an agglutinating agent, said agglutinating agent having at least two binding sites which are common binding sites capable of specifically binding with the carrier reagent, the analyte, and a multivalent ligand;
   (d) a multivalent ligand having at least two binding sites capable of specifically binding with the common binding sites on the agglutinating agent; and
(B) detecting the presence and/or amount of the analyte by determining the resulting decrease in agglutination resulting from the presence of analyte.

DESCRIPTION OF THE INVENTION

This invention is related to an agglutination method to detect and/or quantitate an analyte in a sample which comprises incubating a sample suspected of containing an analyte, a carrier reagent which is a specific binding substance attached to a carrier, an agglutinating agent, the agglutinating agent having at least two binding positions, which are common binding sites capable of specifically binding with the analyte, the carrier reagent, and the multivalent ligand, and, a multivalent ligand having at least two binding sites which are capable of specifically binding with the common binding site or sites of the agglutinating agent, and detecting the presence and/or amount of the analyte by determining the resulting decrease in agglutination resulting from the presence of analyte.

The present invention is based on the unexpected and surprising finding that the presence of a multivalent ligand having two or more binding sites capable of specifically binding with at least two binding sites of an agglutinating agent which are common binding sites which can specifically bind the analyte, the carrier reagent, and the multivalent ligand, results in significant increases in agglutination rates and enhanced assay sensitivity.

The term "analyte" as used herein means any substance having at least one specific binding site which is to be detected and/or quantitated in accordance with the present invention. Examples of analytes which can be determined using the method of the present invention include, but are not limited to, compounds of biological interest found in serum and plasma, salivary, urinary or milk proteins, as well as various haptens, drugs, vitamins, hormones, enzymes, enzyme substrates, antigens, and other proteins, polyclonal and monoclonal antibodies, analogs of antibodies, immunological fragments of antibodies, such as F(ab)$_2$ and F(ab')$_2$ fragments, polysaccharides, bacteria, protozoa, fungi, viruses, antigens, nucleic acids, blood cell or blood fluid substances, and biological cells. Preferred analytes include drugs and those substances for which a quantitative determination is required for the assessment of a disease state. The analyte can be monovalent or multivalent and further can be a monovalent substance which has been rendered multivalent by means of linker, as in for example, a hapten-protein conjugate.

By "monovalent" it is meant a substance having a single specific binding site.

The term "multivalent ligand" as used herein means any substance, other than the carrier reagent, having at least two binding sites which are capable of specifically binding the common binding sites of an agglutinating agent, wherein the agglutinating agent has at least two common binding sites which are capable of specifically binding the analyte, the carrier reagent and the multivalent ligand. Thus the multivalent ligand, the analyte, and the carrier reagent can each specifically bind with the common binding sites on the agglutinating agent. Examples of multivalent ligands include structural analogs of the analyte and derivatives of the analyte. These analogs and derivatives can be characterized as having at least two (dimeric) or more binding sites capable of specifically binding to the common binding sites on an agglutinating agent, wherein the analyte, can also specifically bind with the same common binding sites on the agglutinating agent. Examples of such derivatives include derivatives of antigens having two or more antigenic determinants, and anti-idiotypic antibodies of the antibody of the analyte. An example of a structural analog of an analyte would be oubain, which is a structural analog for digoxin.

A multivalent ligand can be prepared using any process capable of incorporating two or more specific binding sites into the same molecule. A linker may be utilized to join the specific binding sites so as to produce a dimeric or other multivalent ligand. Examples of known processes for the preparation of multivalent ligands include the coupling of activated carboxyl derivatives of a ligand serving as a linker with polyamine groups on substances having specific binding sites. Similarly, coupling methods in which the amino group(s) is initially on the ligand serving as the linker can be used as well. Thus, any method for coupling specific binding substances can be used to prepare the multivalent ligand.

A preferred multivalent ligand is a water soluble molecule in which at least two binding sites are joined by a linking group of sufficient length to permit binding of the multivalent ligand with at least two units of an agglutinating agent. A dimeric multivalent ligand having two binding sites is preferred.

The term "agglutinating agent" as used herein means any multivalent substance having at least two binding sites, which are common binding sites. The common binding site is a binding site on the agglutinating agent which is capable of specifically binding with the analyte, the carrier reagent, and the multivalent ligand. A multivalent substance is one which has at least two binding sites for specific binding. Examples of agglutinating agents include antigens, polyclonal and monoclonal antibodies, analogs of antibodies, immunological fragments of antibodies, such as F(ab)$_2$ and F(ab')$_2$ fragments, antibodies or their immunological fragments attached to carriers, such as particles, or attached to other substances in the form of conjugates, other specific binding proteins such as thyroxine binding globulin, and nucleic acids. As an example, agglutinating agents can include particle-based agglutination agents, such as agglutinating agents in which an antibody of the analyte or an immunological fragment thereof is covalently or non-covalently attached to a particle. Such particle-based agglutinating agents can be employed in a variety of agglutination assay configurations including those in which the specific binding substance is covalently attached to a particle to form a particle based carrier reagent. Preferred agglutination agents are bivalent antibodies or multivalent antigens. The preferred particles for use as particle-based agglutinating agents are those having diameters of less than 0.15 μm. However, larger particles can also be used.

The term "specific binding substance" as used herein means any substance which is capable of specifically binding with the common binding sites on an agglutinating agent, where the common binding sites of the agglutinating agent are capable of specifically binding the analyte, a carrier reagent, and a multivalent ligand. Thus, the specific binding substance, the analyte, and the multivalent ligand can each specifically bind the common binding sites on an agglutinating agent. Examples of specific binding substances include the analyte or a specifically bindable portion thereof, analogs of the analyte, and derivatives of the analyte. A specifically bindable portion of the analyte which can serve as a specific binding substance includes any portion of an analyte which can specifically bind with the common binding sites on the agglutinating agent in the same manner that the analyte can specifically bind the common binding sites on the agglutinating agent and include, for example, specific binding sites of antibodies and other proteins, immunological fragments of antibodies, such as F(ab)$_2$ and F(ab')$_2$ fragments, and antigenic determinants of antigens. Derivatives of the analyte can include, for example, monovalent forms of the analyte which have been rendered multivalent by means of linker, as in for example, a hapten-protein conjugate. Additional examples of specific binding substances include an antigen, an antibody, an immunological fragment, an enzyme, an enzyme substrate, a biological cell, and a nucleic acid. An important feature of the specific binding substance is that it is a substance capable of specifically binding the common binding sites on an agglutinating agent. The preferred specific binding substance is the analyte to be determined.

The specific binding substance can be attached either covalently or non-covalently, with or without the use of a linker, to a carrier to form a carrier agent. In preparing the carrier agent, the specific binding substance must be attached to the carrier in such a manner that subsequent to binding, the specific binding substance, and hence the carrier reagent remains capable of specifically binding the agglutinating agent.

The term "carrier" as used herein means any substance to which a specific binding substance can be attached. The carrier thus facilitates the agglutination reaction by providing a means for multiple specific binding sites (multivalent) for binding with the second member of the specific binding pair. Examples of carriers include soluble substances such as proteins, polysaccharides, synthetic water soluble polymers, synthetic water soluble proteins, and can also include insoluble substances such as latex particles, inorganic particles such as gold sols, pigment particles, and biological cells, such as tanned red blood cells.

The specific binding substance can be attached to the particles by non-covalent means, as for example, by adsorption or coating of the particles, or via covalent means. Covalent attachment is preferred. The surface of a particle can be modified using any of several known processes to produce a surface capable of covalent attachment by any of several alternative chemical techniques. For example, an epoxy group can be hydrolyzed to form a diol compound capable of reacting with cyanogen bromide; the cyanogen bromide can then act as a coupling agent for the amine groups of proteins. Furthermore, aldehydes can react directly with amines to form a Schiff's base which can subsequently be reduced to form a covalent linkage. Alternatively, the aldehyde can be oxidized to an acid and a carbodiimide can be used for subsequent reaction with amines to form an amide linkage.

The specific binding substance can be covalently attached to a particle through a linker. For example, a hapten can be attached to a protein and the resulting conjugate then attached to the particle. Alternatively, the protein can be first attached to the particle, and then the hapten can be attached to the protein. The hapten or proteinaceous material, for example, can be adsorbed onto the surface of the polymer particle followed by the reaction of a functional group, for example, an epoxide group, under suitable pH conditions, with the complementary functional group of the hapten or the proteinaceous material.

The preferred carrier is a light scattering particle to which ligands can be covalently attached. Preferred particles for use as carriers are those having diameters of less than 0.15 μm However, particles of 0.8 μm or more can also be used. Preferably, the particles have a refractive index significantly different from water. Examples of particles that can be used in the practice of this invention include latex particles, gold sol particles, other inorganic particles, and biological cells. Preferred particles for use as carriers in the present invention are high refractive index shell core polymers in which the high refractive index of the core results in high sensitivity to light scattering measurements and the shell contains functional groups to which ligands can be covalently bonded.

The preferred particle reagents of the present invention and the covalent attachment of proteins to them are disclosed in U.S. Pat. Nos. 4,401,765, issued Aug. 30, 1983 and 4,703,018, issued Oct. 27, 1987, the disclosures of which are hereby incorporated by reference. The term "high refractive index shell core polymer particle" as used herein means the particles disclosed in U.S. Pat. Nos. 4,401,765 and 4,703,018 and described below. U.S. Pat. No. 4,401,765, issued Aug. 30, 1983 discloses high refractive index shell core polymers comprising shell core latex particles having a high refractive index polymer core and a polymer shell containing reactive epoxy, carboxyl, amino, hydroxyl, or formyl groups for covalent coupling of proteins. High refractive index shell core polymers comprising shell core latex particles, having diameters of less than 0.15 μm and having a high refractive index polymer core and a polymer shell containing reactive epoxy groups are preferred. These latexes provide a high refractive index core which maximizes light scattering efficiency while also providing selected functional groups for hapten and protein immobilization onto reactive shells. U.S. Pat. No. 4,703,018, issued Oct. 27, 1987 disclose particles which are an improvement over the particles disclosed in U.S. Pat. No. 4,401,765 in that they provide reactive halide groups on the surface of core shell particles.

The desired properties for particles used as carriers in the agglutination based reactions of the present invention depend on the type of light scattering detection means used. The light scattering properties of particle suspensions depend on several variables, including particle size, the refractive indices of the core and the suspension medium, and the wavelength of the light used for measurement. Thus the selection of particle core material, particle size, the refractive indices of the core material and the suspension medium, and the and wavelength of light used for measurement are all important in optimizing assay sensitivity. These factors can be determined by the type of light scattering detection means used. U.S. Pat. No. 4,703,018, issued Oct. 27, 1987, discloses various light scattering measurements and several factors useful in optimizing the light scattering properties of particles depending on the type of light scattering measurement employed, and further discloses the preferred particle reagents of the present invention. In addition to visual detection, various known types of scattering measurements of the agglutination reaction which can be used in the present invention include turbidimetric, nephelometric, particle counting, quasi-elastic light scattering, autocorrelation spectroscopy, and measurements of the dissymmetry or the polarization of the particles.

Turbidimetric measurement is preferred for immunological agglutination reactions since no special equipment is required other than a spectrophotometer. The spectrophotometer measures increased absorbance which is due to the increasing particle size resulting from the agglutination reaction. This increased absorbance is a direct measure of the agglutination caused by the analyte or an indirect measure of the agglutination inhibition caused by the analyte. When light is passed through an agglutinated reaction mixture, part of the incident radiant energy is dissipated by absorption, reflection, and refraction, while the remainder is transmitted. Measurement of the intensity of the transmitted light as a function of the concentration of the dispersed phase is the basis of turbidimetric analysis. For turbidimetric detection, small particles of about 0.03–0.1 micrometers of high refractive index and short wavelength detection (convenient wavelengths are those in excess of 320 nm) are preferred for high sensitivity.

The present invention can be utilized in a wide variety of agglutination-based assay formats which can be designed in any number of ways depending on the type of analyte and the sensitivity required. For example, for analytes in relatively high concentrations, such as certain serum proteins, appropriate antibody particle reagents can be used in direct turbidimetric immuno-precipitation techniques. The present invention can also be practiced using an inhibition assay format as described below.

FIG. 1 is a schematic representation of the present invention for detecting and/or quantitating an analyte (4). The agglutination reaction occurs when the multivalent agglutinating agent (1), such as an antibody, links carrier reagents (2) together to form an agglutinated complex (5). The agglutination reaction is conducted in the presence of a multivalent ligand (3) which is at least dimeric so that the multivalent ligand contains at least two binding sites which are capable of specifically binding with the common binding site on the agglutinating agent. The concentration of the multivalent ligand should be below the concentration at which the multivalent ligand would interfere with the agglutination reaction so as to decrease the rate of agglutination. Preferably the concentration range of the multivalent ligand is of the same order of magnitude range as the concentration of the agglutinating agent.

Figure 2:
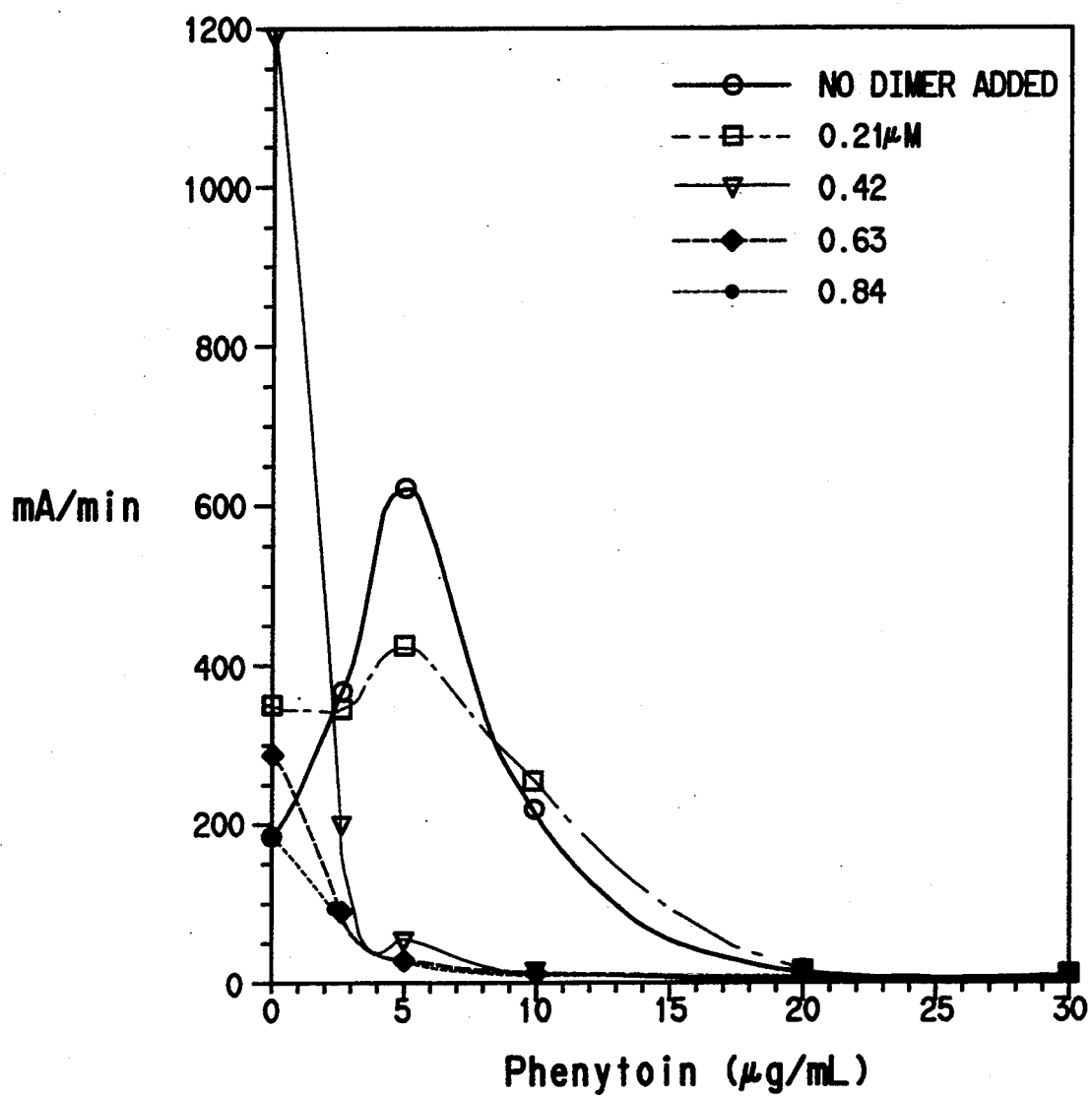
FIG. 2 depicts the results of an assay for phenytoin performed in the presence of various concentrations of a phenytoin dimer, in which the agglutination was measured using a Cobas Bio ® centrifugal analyzer (Roche Analytical Instruments, Inc., Nutley, N.J.); the agglutination reaction was initiated upon addition of the carrier reagent. Assay response, shown in mAU/min, was determined from the change in absorbance seen in the time interval from 50 to 60 seconds after initiation of the reaction.
Figure 3:
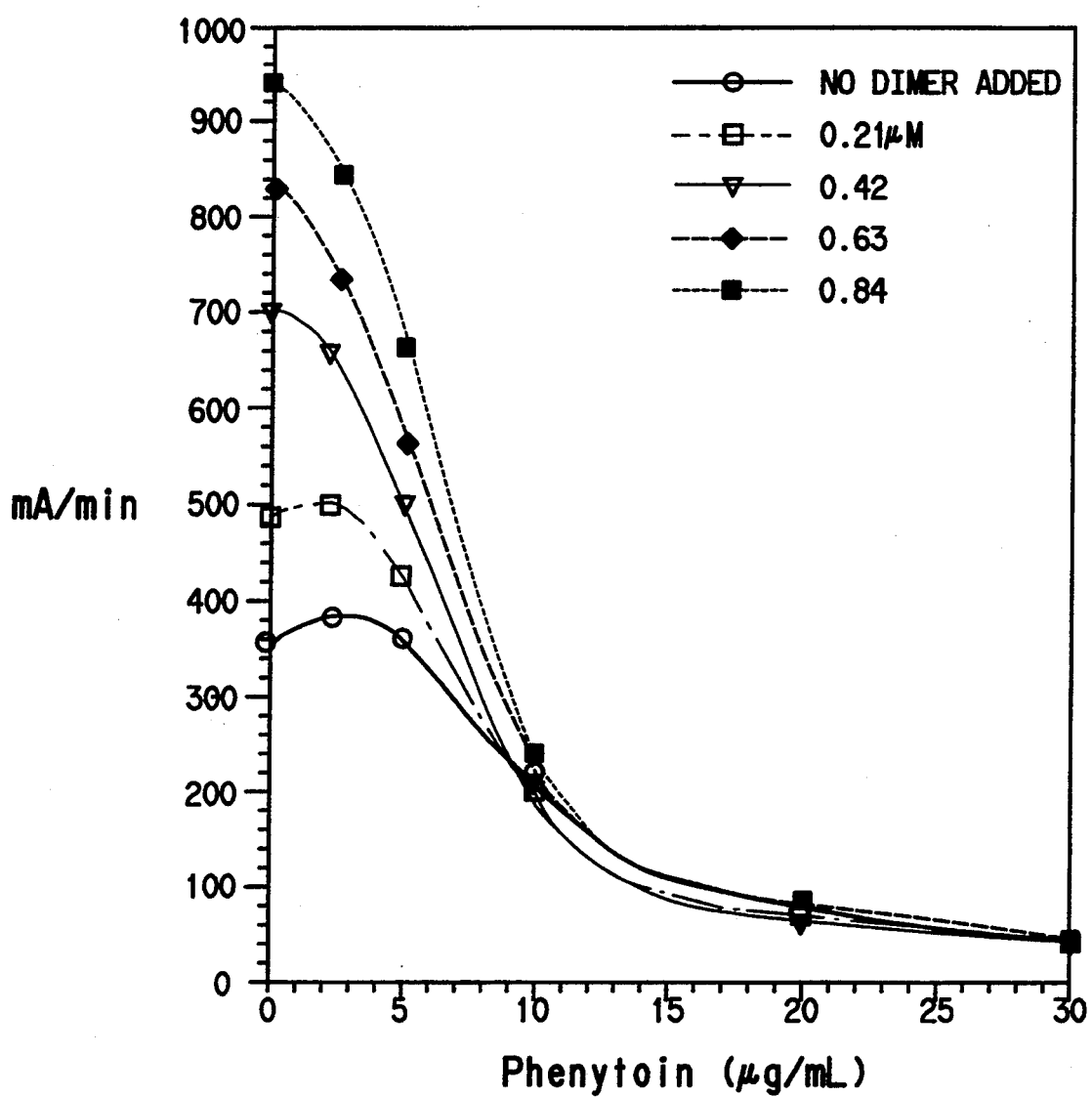
FIG. 3 depicts the results of an assay for phenytoin performed in the presence of various concentrations of a phenytoin dimer, in which the agglutination was measured using a Cobas Bio ® centrifugal analyzer (Roche Analytical Instruments, Inc., Nutley, N.J.); the agglutination reaction was initiated upon addition of the agglutinating agent. Assay response, shown in mAU/min, was determined from the change in absorbance seen in the time interval from 0 to 60 seconds after initiation of the agglutination reaction.

The sample suspected of containing the analyte, the multivalent ligand, the agglutinating agent, and the carrier reagent can be incubated together following any sequence of addition. For example, the carrier agent can be added to a vessel containing the agglutinating agent, the multivalent ligand, and the sample (FIG. 2), or the agglutinating agent can be added to a vessel containing the multivalent ligand, the carrier reagent, and the analyte (FIG. 3). Preferably, the carrier reagent is added after the agglutinating agent, the multivalent ligand, and the sample are mixed together (FIG. 2).

The preferred embodiment of the present invention is a competitive particle enhanced turbidimetric inhibition immunoassay in which the carrier is a latex particle to which is covalently attached a specific binding substance which is the analyte, the analyte is an antigen or hapten such as a drug, and the multivalent ligand is a dimeric substance having two binding sites coupled via a linker which are capable of specifically binding the common binding site on an agglutinating agent, such as an antibody, which can specifically bind the analyte, the carrier reagent, and the multivalent ligand. In an inhibition format, the analyte competes with the carrier reagent for the common specific binding site on the agglutinating agent, thus reducing the extent of agglutination.

For the measurement of drug analytes such as haptens, several different assay configurations can be used. In one such configuration, antigenic particle reagents serving as the carrier reagent can be prepared by attaching either haptens or hapten-protein conjugates to a polymer particle to form hapten-particle or hapten-protein-particle reagents. The inhibition of the agglutination reaction between these particle reagents and the specific binding sites on appropriate antibodies by the hapten can then be determined. The agglutination reaction can be performed by direct competition of the particle carrier reagent and the sample hapten for the antibody or by the reaction of the hapten with antibody followed by the addition of the particle reagent.

The following example illustrates the invention.

EXAMPLE (A) Synthesis Of A Phenytoin (PTN) Linker Intermediate For Synthesis Of A PTN Dimer Multivalent Ligand)

Carboxy butyl diphenylhydantoin (CBDH) was synthesized by the alkylation of ethyl bromopentanoate using a procedure substantially similar to that described in U.S. Pat. 3,905,871, Rubenstein, et al., the disclosure of which is hereby incorporated by reference. CBDH was then converted to the N-hydroxysuccinimide ester and conjugated to a water soluble diamine linker as shown below:

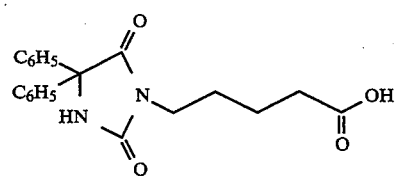

Carboxy butyl diphenylhydantoin
(CBDH)

+

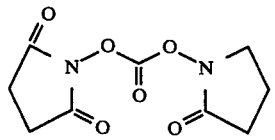

Disuccinimidyl carbonate
(DSC)

| Triethylamine
(TEA)

from the reaction mixture using a rotary evaporator and the residue was then triturated with 250 mL of ice-water, filtered, and dried in vacuo. Crude product yield was 4408 mg (98%). The crude product was then recrystallized from 250 mL of isopropanol, filtered and dried in vacuo. Recovery of the purified product, which was determined to have a melting point of 185°–186° C., was greater than 90%.

(B) Synthesis Of A CBDH/DA-10 Conjugate For Covalent Bonding With a Latex Particle A CBDH DA-10 conjugate was synthesized using the reaction scheme shown below.

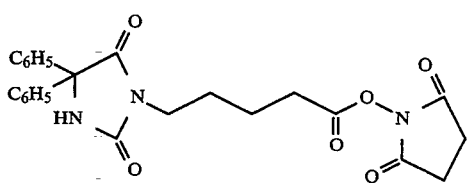

CBDH N-hydroxysuccinimide ester
(PTN Linker Intermediate)

+

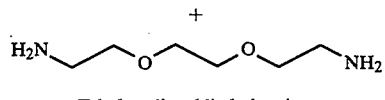

Ethylenedioxyldiethyl amine
(DA-10)

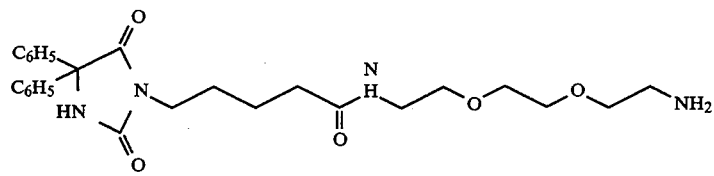

CBDH/DA-10 Conjugate

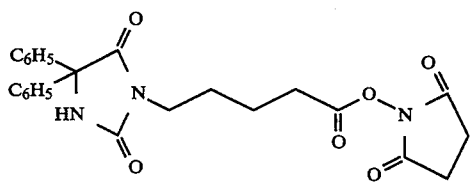

CBDH N-hydroxysuccinimide ester
PTN Linker Intermediate)

3524 mg (10.00 mmole) CBDH and 2818 mg (11.00 mmole) of disuccinimidyl carbonate (DSC) were mixed with 50 mL of dry tetrahydrofuran (THF) in a round, 300-mL, one-necked flask provided with a magnetic stirrer bar and maintained under a dry atmosphere. After mixing for about 15 minutes (some portion of the DSC remained-undissolved) 1394 μL (10.00 mmoles) of triethylamine (TEA) was added to the flask and the mixture stirred for an additional 1.5 hours, during which time the DSC was observed to slowly dissolve completely. The solvent was subsequently removed A solution of 0.6 mL of ethylenedioxydiethyl amine (hereinafter referred to as DA-10, for 10 atom diamine linker) in 5 mL of DMSO was added to 450 mg of CBDH/NHS ester in 5 mL with rapid stirring at room temperature for five minutes.

The resulting CBDH/DA-10 conjugate was subsequently used for covalent bonding to the surface of latex particles. The CBDH/DA-10 conjugate was covalently bonded to particles using the particles and procedure disclosed in U.S. Pat. No. 4,401,765, the disclosure of which is hereby incorporated by reference. The particles used were high refractive index shell core polymers comprising shell core latex particles having diameters of approximately 0.06–0.07 μm and further having a high refractive index polymer core and a polymer shell containing reactive epoxy groups.

(C) Synthesis OF A PTN Dimer For Use As A Multivalent Ligand

A PTN dimer was prepared using the Phenytoin PTN-Linker Intermediate described in (A) above and as shown below:

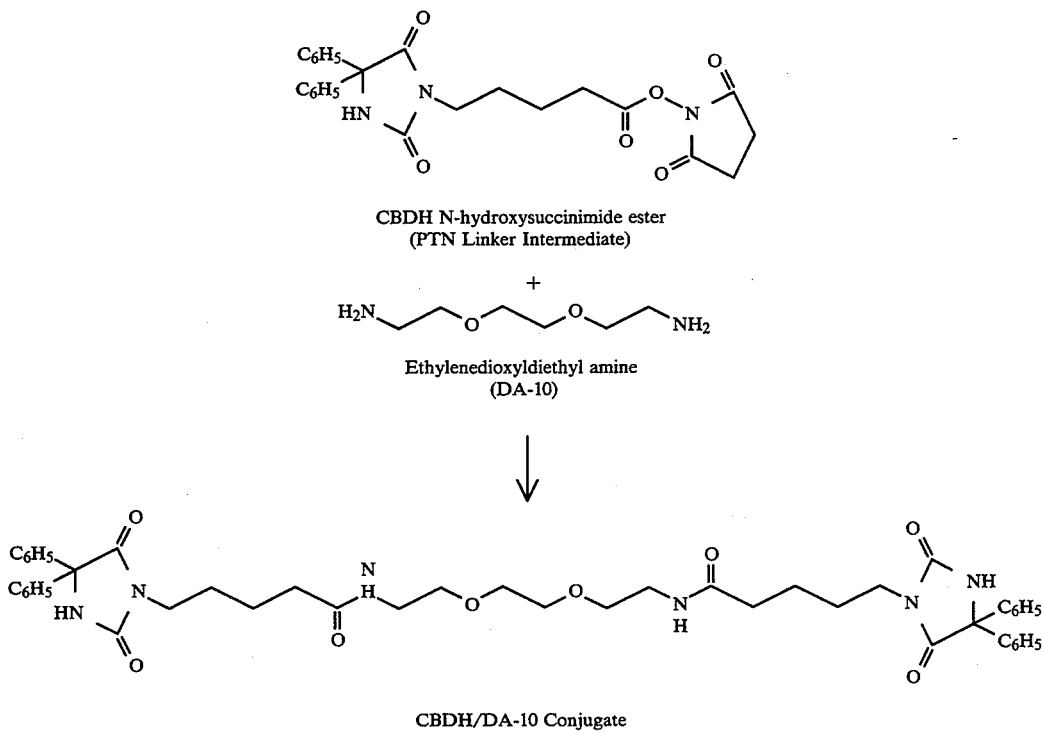

CBDH/DA-10 Conjugate

A mixture of 981 μL dry DMSO, 3.7 mL DA-10, and 7.2 μL dry triethylamine was mixed with a solution of 22.5 mg CBDH/NHS ester in 997 μL dry DMSO to achieve a final concentration of 25 mmolar for the CBDH dimer (equivalent to 6.3 mg/mL stock of PTN in terms of binding concentration).

(D) Preparation Of A PTN Particle Reagent 2 mL concentrated polystyrene/polyglycidyl methacrylate latex particles, which were high refractive index shell core polymers comprising shell core latex particles having diameters of approximately 0.06–0.07 μm and further having a high refractive index polymer core and a polymer shell containing reactive epoxy groups (as described in U.S. Pat. No. 4,401,765, were added to a mixture of 0.12% GAFAC RE610 (GAFAC) detergent (commercially available as Rhodofac from Rhone-Poulenc, Inc. Monmouth Junction, N.J. 08852). 0.2 mL of the CBDH/linker amine conjugate (described in (C) above) was added and the pH of the mixture adjusted to pH 10.0 with 0.1N NaOH. The mixture was then heated for two hours at 70° C. After two hours, any unreacted compounds with PTN activity were removed by repeated centrifugation. The reaction mixture was then diluted in 30 mM pH 7 sodium phosphate buffer containing 1% GAFAC, and the latex particles separated by centrifugation. The pellet was resuspended in the same buffer, and the centrifugation procedure repeated three additional times.

(E) Phenytoin Assay

Assays were performed at 37° C. using a Cobas Bio ® centrifugal analyzer (Roche Analytical Instruments, Inc., Nutley, N.J.).

The samples which were used contained the analyte phenytoin and were commercially available calibrators used with the Du Pont aca ® Clinical Chemistry System (E. I. du Pont de Nemours and Company, Wilmington, Del.).

A reagent buffer was prepared as follows. A solution of 12.5 mM PTN dimer in DMSO was prepared using the process described in step (C). This solution with diluted with a buffer solution composed of 0.25% GAFAC in 130 mM dibasic sodium phosphate adjusted to pH 7.0 to make a solution of 10.0 μM PTN dimer. This 10.0 μM solution was further diluted to final stocks of reagent buffer having PTN dimer concentrations as shown in Tables 2 & 3. The reagent buffer also contained either the agglutinating agent (see section F) or the carrier reagent (see section G) as described below. A 300 μL volume of reagent buffer was used in each of the assays performed.

A start reagent was prepared containing a buffer solution composed of 0.25% GAFAC in 130 mM dibasic sodium phosphate adjusted to pH 7 and either the carrier reagent (see section F) or the agglutinating agent (see section G) as described below. A 20 μL volume of start reagent was used in each of the assays performed.

In the procedure described in (F) the reagent buffer contained the agglutinating agent and the start reagent contained the carrier reagent. In the procedure described in (G) the reagent buffer contained the carrier reagent and the start reagent contained the agglutinating agent.

In both procedures (F) and (G) below, the amount of particle reagent used was determined experimentally. The particle concentration was adjusted to give an optical density in the assay of approximately 0.85 AU.

A 3 μL sample was used for each of the assays performed. For comparison, when 3 μL of a 5 μg/mL phenytoin sample calibrator is assayed using the Cobas ® centrifugal analyzer the concentration of phenytoin that results is 0.165 μM.

The agglutinating agent used was an anti-phenytoin monoclonal antibody F(ab')2 fragment prepared by pepsin digest of a monoclonal antibody to phenytoin. The anti-phenytoin monoclonal antibody was prepared using procedures for the preparation of monoclonal antibodies such as that described in Kohler and Milstein, Nature, volume 256, 495–497 (Aug. 7, 1975), the disclosure of which is hereby incorporated by reference. Any antibody or fragment thereof which is capable of serving as an agglutinating agent, that is one that can specifically bind with the analyte phenytoin, the carrier reagent, and the multivalent ligand PTN dimer through its common binding sites can be used in the method of the present invention.

The Cobas ® centrifugal analyzer was programmed to mix 3 μL of the sample, 20 μL of water used as a diluent, and 300 μL of reagent buffer, and to incubate them for two minutes at 37° C. After this period, 20 μL of start reagent (see procedure F or G below) was added, and the optical density was measured at ten second intervals after the last addition. The change in optical density with time is reported as mAU/min, and was determined as described below.

(F) Phenytoin Agglutination Reaction Initiated by the Addition of a Carrier Reagent In this assay format, the reagent buffer contained the agglutinating agent to make a final agglutinating agent concentration of approximately 30–60 μg/mL. The reaction was initiated by the addition of a particle based carrier reagent. The carrier reagent was prepared as described in (B) above. In the Table 1 below, the assay response is recorded in units of mAU/min, which was obtained by multiplying by six the change of absorbance from 50 to 60 seconds after initiation of the reaction.

TABLE 1

| PTN (μg/mL) | PTN Dimer (μM) | | | | |
|---|---|---|---|---|---|
| | 0 | 0.21 | 0.42 | 0.63 | 0.84 |
| | Absorbance rate (mAU/min) | | | | |
| 0 | 181 | 348 | 1185 | 286 | 183 |
| 2.5 | 366 | 347 | 197 | 94 | 91 |
| 5 | 617 | 422 | 60 | 30 | 37 |
| 10 | 211 | 245 | 11 | 11 | 15 |
| 20 | 18 | 15 | 9 | 2 | 4 |
| 30 | 6 | 9 | 0 | 0 | 5 |

It can be seen from Table 1 that the assay does not give a satisfactory standard curve in the absence of PTN dimer. In the presence of 0.42 μM dimer, the assay is very sensitive to phenytoin, and the aggregation, as measured by the rate of change of turbidity, is relatively fast. At higher concentrations of dimer, the performance of the assay is not as sensitive or fast.

FIG. 2 depicts in graphic form the results shown above in Table 1.

(G) Phenytoin Agglutination Reaction Initiated by the Addition of an Agglutinating Agent In this assay format the reagent buffer contained the carrier reagent so that the particle concentration was adjusted to give an optical density in the assay of approximately 0.85 AU. The reaction was started with a sample of agglutinating agent at a concentration such that the concentration the assay concentration was the same as in (F). In Table 2 below, the assay response is recorded in units of mAU/min, which was obtained from the change of absorbance from 0 to 60 seconds after initiation of the agglutination reaction.

TABLE 2

| PTN (μg/mL) | PTN Dimer (μM) | | | | |
|---|---|---|---|---|---|
| | 0 | 0.21 | 0.42 | 0.63 | 0.84 |
| | Absorbance rate (mAU/min) | | | | |
| 0 | 356 | 489 | 702 | 831 | 935 |
| 2.5 | 382 | 493 | 654 | 730 | 840 |

TABLE 2-continued

| PTN (μg/mL) | PTN Dimer (μM) | | | | |
|---|---|---|---|---|---|
| | 0 | 0.21 | 0.42 | 0.63 | 0.84 |
| | Absorbance rate (mAU/min) | | | | |
| 5 | 357 | 420 | 502 | 563 | 657 |
| 10 | 211 | 194 | 196 | 238 | 236 |
| 20 | 76 | 70 | 70 | 86 | 80 |
| 30 | 44 | 36 | 37 | 36 | 42 |

It can be seen from Table 2 that the assay does not provide a satisfactory standard curve in the absence of PTN dimer. In the presence of 0.84 μM dimer, the assay is more sensitive to phenytoin, and the aggregation as measured by the rate of change of turbidity is relatively fast. At higher concentrations of PTN dimer, the performance of the assay is not as good.

FIG. 3 depicts in graphic form the results shown above in Table 2.

What is claimed is:

1. A competitive agglutination method to detect and/or quantitate an analyte in a sample which comprises:
    (A) incubating
        (a) a sample suspected of containing said analyte,
        (b) a carrier reagent which comprises a specific binding substance attached to a particle, wherein said specific binding substance specifically binds to a non-particulate agglutinating agent,
        (c) the non-particulate agglutinating agent which comprises at least two common binding sites which specifically bind the specific binding substance of the carrier reagent, the analyte, and a soluble multivalent ligand,
        (d) the soluble multivalent ligand which comprises at least two binding sites which specifically bind the common binding sites of the non-particulate agglutinating agent and which are joined by a linking group of sufficient length to permit binding of the multivalent ligand with at least two units of the non-particulate agglutinating agent, wherein said soluble multivalent ligand 1) does not specifically bind to the specific binding substance of the carrier reagent and 2) is present in a concentration below that which would interfere with an agglutination reaction,
    wherein the analyte competes with the carrier reagent for the common specific binding sites on the non-particulate agglutinating agent, thus reducing the extent of agglutination;
    (B) detecting or measuring the resulting agglutination; and
    (C) relating the extent of inhibition of agglutination resulting from the presence of analyte in the sample to the presence and/or amount of the analyte.

2. The method according to claim 1 wherein the particle of the carrier reagent is selected from the group consisting of latex particles, inorganic particles, and biological cells.

3. The method according to claim 1 wherein the particle is a high refractive index shell core polymer particle.

4. The method of claim 1 wherein the specific binding substance of the carrier reagent is covalently attached to the particle.

5. The method of claim 1 wherein the specific binding substance of the carrier reagent is attached to the particle through a linker.

6. The method according to claim 1 wherein the non-particulate agglutinating agent is selected from the group consisting of an antigen, an antibody or an immunological fragment thereof, an enzyme, and enzyme substrate, and a nucleic acid.

7. The method according to claim 1 wherein the specific binding substance of the carrier reagent is selected from the group consisting of an antigen, an antibody or an immunogical fragment thereof, a hapten, an enzyme, and enzyme substrate, a biological cell, and a nucleic acid.

8. The method according to claim 1 wherein the soluble multivalent ligand is selected from the group consisting of structural analogs of the analyte, derivatives of the analyte, and anti-idiotypic antibodies of an antibody which specifically binds to the analyte.

9. The method according to claim 1 wherein the multivalent ligand is dimeric.

10. The method according to claim 1 wherein the extent of inhibition of agglutination is measured photometrically.

* * * * *